United States Patent [19]

Mikkelsen

[11] Plant 5,158

[45] Dec. 13, 1983

[54] BEGONIA PLANT NAMED ENCORE

[75] Inventor: James C. Mikkelsen, Ashtabula, Ohio

[73] Assignee: Mikkelsens, Inc., Ashtabula, Ohio

[21] Appl. No.: 418,489

[22] Filed: Sep. 15, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia named Encore having bright pink double flowers, dark green, firm to crisp glabrous foliage with sharp and distinct serrated edges; above average keeping qualities, and having continuous year round flowering.

1 Drawing Figure

The present invention relates to a new and distinctive cultivar of begonia plant, botanically known as hiemalis begonia (Fotsch), and referred to by the cultivar name Encore.

The new cultivar was discovered by me as a seedling from a controlled crossing in Ashtabula, Ohio of tuberous hybrida 76-177-2 as the seed parent with selected Socotrana 74-248-S as the pollen parent. Asexual reproduction by leaf cuttings in Ashtabula, Ohio has reproduced the unique features of the new cultivar through successive propagations.

The following characteristics distinguish the new begonia from both its parent and other begonias commercially known and used in the floriculture industry:

1. Tuberous seedling 76-117-2 had large double deep pink flowers, large leaves with heavy pubescense and early flower drop. Encore has distinct orbicular cleft leaves with sharp serration, its flowers are double with ruffled edges, and it has light pink tepals.

2. The pollen parent Socotrana has light green foliage and light pink single type flowers. The flower color of Encore is similar to flower color of Socotrana.

3. In comparison to Riegers Elfe (U.S. Plant Pat. No. 4,125), the flower color of Encore is sharp clear pink, flowers are more double and the leaves more distinct.

4. Encore foliage is unique, with sharp serrations that are retained through maturity of the leaf. Foliage is crisp yet not brittle.

5. Encore is above average in numbers of flowers produced per stem. The keeping quality of flowers is excellent, and the flower color is a clear pleasing pink.

6. Propagation by leaf cuttings is extremely good, consistently producing 5–6 or more adventitious shoots per petiole. Total propagation time is slower by 7–10 days than many present commercial cultivars.

7. Plant growth is also somewhat slower so that Encore is more ideally suited for 10–12 cm. pots than larger containers. Highly sensitive to normal rates of growth regulators Cycocel and A-Rest.

8. Encore has exceptional keeping qualities for both foliage and flowers, making it ideal for mass distribution.

The accompanying colored photograph taken December, 1981 illustrates in perspective view the overall appearance of Encore grown in a 12 cm. clay pot, and showing the colors as true as it is reasonably possible to obtain in a colored reproduction of this type.

The following is a detailed description of my new begonia cultivar based on plants produced under commercial practices at the greenhouses of Mikkelsens Inc., Ashtabula, Ohio 44004. Color references are made to The Royal Horticultural Society Colour Chart except where general color terms of ordinary dictionary significance are used.

Parentage: A controlled cross of my tuberious hybrida seedling 76-117-2 with a selected inbred seedling of Socotrana 74-248-S.

Propagation:

(A) *Type cutting.*—Leaf cuttings.

(B) *Time to root.*—25–28 days at 21° C. summer, 30–35 days at 21° C. winter.

(C) *Rooting habit.*—Abundant, fibrous, dendritic.

(D) *Time for shoot development.*—Shoot initiation and development is slow, taking up to 12 weeks in summer to 15 weeks in winter. Shoot count is high per leaf cutting.

Plant description:

(A) *Form.*—Low, compact, bush type plant; herbaceous.

(B) *Habit of growth.*—Sturdy, upright slow growth with considerable self-branching, combined with good adventitious shoot count make a well rounded uniform looking plant.

(C) *Foliage.*—Simple, alternate, borne on strong semi-rigid petioles. (1) Size: Generally small, up to 6–8 cm. from base to apex. (2) Shape: Orbicular cleft serrated having an appearance of maple leaf. (3) Texture: Firm, crisp but not brittle, glabrous on top, rugose underside. (4) Margin: Serrated. (5) Color: Young foliage top side, green 137A; under side, red 181A with green veins protruding; Mature foliage top side green 137A with slight red overtone; under side, yellow green 148B with red pigmentation. (6) Venation: Palmate.

Flowering description:

(A) *Flowering habit.*—Flowering is presented in a raceme, with flowering continuing with secondary buds developing below the primary flowers.

(B) *Natural flowering season.*—Generally flowers year round after developing some maturity. Once flowering has initiated, plants will continue to flower up to twelve months.

(C) *Flower bud description.*—Flat, nearly round, tending to heart-shape.

(D) *Flowers borne.*—On small but sturdy pedicels originating from strong peduncles result in the raceme form of terminal flower blooming first and additional flowering progressing as raceme develops.

(E) *Quantity.*—Flowering is abundant with 12–15 flowers open at one time per peduncle.

(F) *Tepals.*—(1) Shape: Slightly oval. (2) Color: Top side in winter when opening; 2 basal tepals red 37B, interior tepals red 49A, fading to red 49B to 38C, under side tight bud red 38A to diluted red 49A. (3) Number of tepals: Generally 12. (4) Size of tepals: Basal tepals 2 to 2.5 cm. (5) Flower size: 3.5 to 4 cm.

(G) *Reproductive organs.*—A sterile triploid.

Disease resistance: To date the new cultivar appears to be highly resistant to powdery mildew when produced in areas of other begonias infected with this problem.

I claim:

1. A new and distinct cultivar of begonia named Encore, as described and illustrated, and particularly characterized by its bright pink double flowers, dark green, firm to crisp glabrous foliage with serrated edges; excellent keeping qualities, and by its continuous year round flowering.

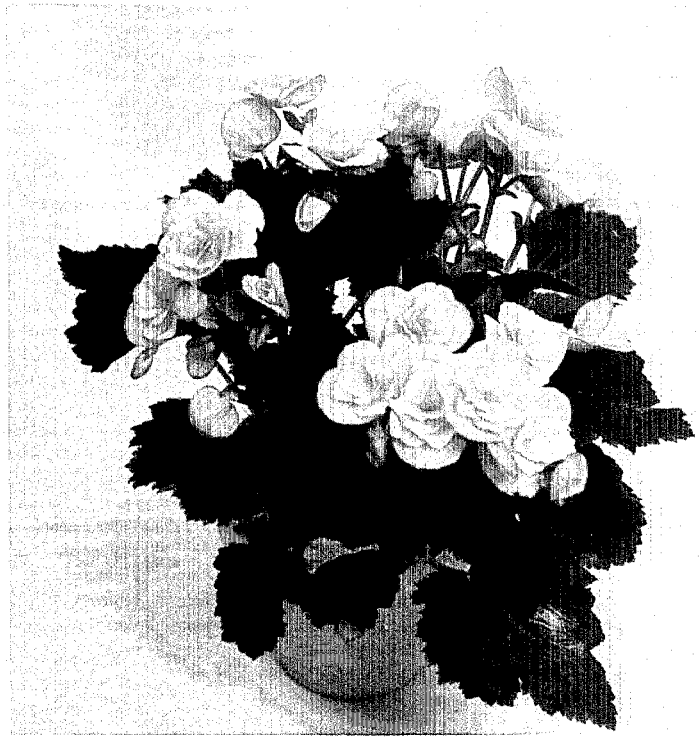

* * * * *